US010076500B2

(12) United States Patent
Grenier et al.

(10) Patent No.: US 10,076,500 B2
(45) Date of Patent: Sep. 18, 2018

(54) FLOATING GASTRIC RETENTIVE DOSAGE FORM

(71) Applicant: Jagotec AG, Muttenz (CH)

(72) Inventors: Pascal Grenier, Kappelen (FR); Alain Nhamias, Bartenheim (FR); Guy Vergnault, Kembs (FR)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 15/072,938

(22) Filed: Mar. 17, 2016

(65) Prior Publication Data

US 2016/0263045 A1 Sep. 15, 2016

Related U.S. Application Data

(63) Continuation of application No. 13/704,760, filed as application No. PCT/EP2011/061257 on Jul. 4, 2011, now Pat. No. 9,314,430.

(30) Foreign Application Priority Data

Jul. 5, 2010 (GB) .................................. 1011271.2
Nov. 9, 2010 (GB) .................................. 1018917.3

(51) Int. Cl.
*A61K 9/48* (2006.01)
*A61K 9/00* (2006.01)
(Continued)

(52) U.S. Cl.
CPC .......... *A61K 9/4808* (2013.01); *A61K 9/0065* (2013.01); *A61K 9/485* (2013.01);
(Continued)

(58) Field of Classification Search
CPC .... A61K 9/0065; A61K 9/4808; A61K 9/485; A61K 9/4891; A61K 9/5047;
(Continued)

(56) References Cited

U.S. PATENT DOCUMENTS 3,976,764 A 8/1976 Watanabe et al.
4,055,178 A 10/1977 Harrigan
(Continued)

FOREIGN PATENT DOCUMENTS

JP 55-12411 B2 4/1980
JP S6322014 A 1/1988
(Continued)

OTHER PUBLICATIONS

Bardonnet, P. L., et al. (Mar. 2006, e-published Jan. 5, 2006). "Gastroretentive dosage forms: overview and special case of Helicobacter pylori," *Journal of Controlled Release* 111 (1-2):1-18.
(Continued)

*Primary Examiner* — Michael B. Pallay
(74) *Attorney, Agent, or Firm* — Mintz Levin Cohn Ferris Glovsky and Popeo, P.C.; Muriel Liberto, Esq.

(57) ABSTRACT

An elongate dosage form of generally cylindrical shape having two opposing ends, the dosage form being buoyant in gastric fluid, wherein the dosage form is weight biased such that one end is heavier than the other end. The dosage form is adapted to float on gastric fluid with its long axis substantially perpendicular to the surface of the fluid with its heavier end pointing generally downwards and into the fluid.

26 Claims, 5 Drawing Sheets

Figure 1:
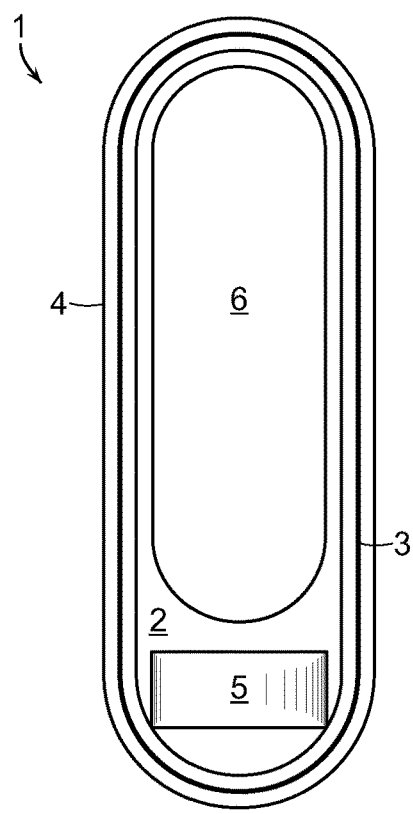

(51) Int. Cl.
*A61K 9/50* (2006.01)
*A61K 31/05* (2006.01)
*A61K 31/4045* (2006.01)
*A61K 31/404* (2006.01)
*A61K 31/454* (2006.01)

(52) U.S. Cl.
CPC .......... *A61K 9/4891* (2013.01); *A61K 9/5047* (2013.01); *A61K 31/05* (2013.01); *A61K 31/404* (2013.01); *A61K 31/4045* (2013.01); *A61K 31/454* (2013.01)

(58) Field of Classification Search
CPC .. A61K 31/05; A61K 31/404; A61K 31/4045; A61K 31/454
See application file for complete search history.

(56) References Cited

U.S. PATENT DOCUMENTS

| | | | |
|---|---|---|---|
| 5,198,229 A | 3/1993 | Wong et al. | |
| 5,417,682 A * | 5/1995 | Wong | A61K 9/4808 604/892.1 |
| 9,314,430 B2 | 4/2016 | Grenier et al. | |
| 2003/0194429 A1 | 10/2003 | Miller | |
| 2006/0239953 A1 | 10/2006 | Clapp et al. | |
| 2014/0227356 A1 | 8/2014 | Kim et al. | |

FOREIGN PATENT DOCUMENTS

| | | | |
|---|---|---|---|
| JP | 2001-514211 A | 9/2001 | |
| WO | WO-99/11246 A1 | 3/1999 | |
| WO | WO-01/97783 A1 | 12/2001 | |
| WO | WO 2004056336 A2 * | 7/2004 | .......... A61K 9/5078 |
| WO | WO-2005/048947 A2 | 6/2005 | |
| WO | WO-2005/048947 A3 | 6/2005 | |
| WO | WO-2010/020098 A1 | 2/2010 | |

OTHER PUBLICATIONS

Chinese Re-Examination Notification dated May 29, 2015, for Chinese Patent Application No. 201180033120.6, filed on Jul. 4, 2011, with English language summary, 8 pages.

* cited by examiner

FLOATING GASTRIC RETENTIVE DOSAGE FORM

The present invention is concerned with a pharmaceutical dosage form, in particular a dosage form that is adapted for prolonged gastric residence time.

Oral drug delivery is generally regarded as the most convenient route for drug administration. However, for many drugs, the plasma levels and duration of effect that can be achieved by the oral route are often limited by the fact that significant drug absorption can only occur in a relatively short section of the upper gastro-intestinal tract, in particular the portion of the gastro-intestinal tract that is proximal to the small intestine e.g duodenum. Drug substances having such narrow absorption sites, are said to exhibit an absorption window.

If therapeutic plasma levels of a drug substance are possible only for a short period of time because of an absorption window, one can attempt to address the problem by increasing dosage frequency. However, administering drug substances via multiple administrations can lead to patient compliance issues, as well as fluctuations in blood plasma levels depending on how rigidly a patient adheres to a dosage regimen.

Given that absorption windows tend to occur in the upper gastro-intestinal tract and more particularly in the region of the intestine proximal to the stomach, to overcome these problems gastro-retentive dosage forms have been developed. These dosage forms attempt to retain a drug substance in the stomach in order to hold it above its absorption site in the upper gastro-intestinal tract for prolonged periods of time and to release the drug at an appropriate rate. In this way, all, or substantially all, of the drug substance will pass in an absorbable form across the absorption window.

In the literature a number of concepts for gastro-retention have been proposed.

One approach for gastric retention involves the use of high density materials. Such dosage forms use their density as a means of retention. When a device is denser than gastric juices in which it is placed it will settle into the bottom of the stomach and be retained in the folds and the mucus of the stomach wall.

Another approach involves the use of bioadhesive coatings applied to dosage forms that stick to mucosal surfaces in the stomach. Quite often, however, prolonged contact between a dosage form and the mucosa can lead to local irritation or even necrosis of tissues.

Still another approach of retaining a dosage form in the stomach is to employ a dosage form that increases its size and reduces its density after administration in response to its contact with gastric media, to form large, low density dosage form that floats on the contents of the stomach.

Large, floating dosage forms are desirable for two reasons. By remaining at the surface of the contents of the stomach, such a dosage form will be delayed in reaching the pyloric sphincter. Furthermore, once at the pyloric sphincter its passage will be hindered because of its large size.

It is known that objects having a size of up to about 7 mm can exhibit delayed release in fed conditions because they are able to float on the contents of the stomach. However, such objects are liable to be emptied rapidly from the stomach because their size is smaller than the opening to the pyloric sphincter. The open pyloric sphincter has a diameter of approximately 12 to 15 mm in humans.

It has been reported that objects of about 12 to 18 mm diameter would generally resist passage from the pyloric sphincter in the fed state. If such an object was able to float and retain its size in gastric fluid under agitation for prolonged periods of time it would be possible for such objects to remain in the stomach after food has passed and resist passage through the sphincter until the commencement of the inter-digestive migrating motor complex. This motor complex is essentially a house keeping phase of the digestive process consisting of a series of muscular contractions designed to sweep larger undigested particles from the stomach. This can occur up to 2 hours after ingestion of food.

Large floating dosage forms known in the art are typically initially rather small in order that they can be swallowed, but are adapted to expand and lower their density upon administration in response to contact with gastric fluid. Specific examples include dosage forms that unfold in the stomach, or otherwise incorporate swellable excipients or excipients that generate gas to effect expansion. Such dosage forms are not without drawbacks, however. There remains a danger that such dosage forms will malfunction and expand before reaching the stomach. Furthermore, if the dosage forms expand too much, there is a concern that they could resist passage to such a degree that they would accumulate in the stomach and cause blockage.

Large floating dosage forms are known, which do not rely on expansion, but which derive their buoyancy by means of comprising a hollow core which traps air or other gases. Typically, such dosage forms consist of large hollow capsules. In the design of such capsules, it is important that they should not be so large as to be uncomfortable or difficult to swallow. However, even very large capsules that will float, such as a size #00, has a width of less than 10 mm, which is small enough to pass relatively rapidly through the pyloric sphincter despite its relatively long length.

There remains a need to provide gastric-retentive dosage forms that are both buoyant as to float on the contents of the stomach, and sufficiently large as to resist passage through the pyloric sphincter. At the same time the dosage form should be sufficiently compact as to be easily swallowed by a patient. Finally, said dosage form should not rely on expansion/reduction of density upon ingestion to achieve its size and buoyancy.

Applicant has now found that an elongate dosage form, such as a capsule, whose length along its long axis is larger than the diameter of the pyloric sphincter, weighted at one end with an appropriate weighting agent such that it floats in an aqueous fluid not with its long axis parallel to the surface of the fluid, but rather substantially perpendicular to it, is able to float and resist passage through the pyloric sphincter notwithstanding that the diameter of said dosage form may be sufficiently small as to pass through the sphincter. In other words, the dosage form resists passage through the sphincter not based on its size, but on its size combined with its ability to orientate itself appropriately in gastric fluid.

The invention provides in one of its aspects an elongate dosage form of generally cylindrical shape having two opposing ends, the dosage form being buoyant in gastric fluid, wherein the dosage form is weight biased such that it is heavier at one end than the other end.

The length of the elongate dosage form according to the present invention along its long axis, is such that it is larger in this particular dimension than the average diameter of the pyloric valve in humans. Preferably, the dosage form is at least 12 mm in length and is more preferably 15 mm or greater along this axis. The upper limit for the length along this axis is determined by what is comfortable to be swallowed by a human patient. Preferably, the dosage form in this dimension is not longer than about 30 or 31 mm.

The dosage form according to the invention may be in any form convenient for oral administration by a human subject. The dosage form may be in the form of a tablet or a capsule, more particularly a hollow capsule.

Capsules are available in a wide variety of types and any capsule for pharmaceutical use is contemplated for use in the present invention. Capsules include hard gelatin capsules, soft elastic capsules, or hydroxypropylmethylcellulose (HPMC) capsules. Examples of capsules include a gelatin capsule such as the CONI-SNAP capsule (trade name, commercially available from CAPSUGEL AG, a Pfizer company), a corn starch capsule such as CAPILL (trade name, commercially available from Warner-Lambert Company, U.S.A.), a hydroxypropylmethylcellulose capsule such as HPMC capsule (trade name, commercially available from Japan ELANCO CO. LTD., Japan) and the like. Among these, a gelatin capsule and a hydroxypropylmethylcellulose capsule are preferable.

Typically capsules consist of two hemispheres, which are formed to cooperate such that one can slip over the other to form a sealed whole. After a capsule has been formed and filled it can be welded or banded at the join between the hemispheres to effect a seal.

Although originally designed for liquid filling, LICAPS capsules from Capsugel with specially designed body shape for sealing with LEMS™ (Liquid Encapsulation Microspray Sealing) to ensure a high level of tightness, are a preferred option for the invention. The LEMS method is well known in the art and needs no detailed discussion here. Briefly, to seal a capsule together, a solution containing water and alcohol may be sprayed between the parts to be sealed in order to lower the melting point of gelatine then with gentle heating solvent is evaporated and fusion of the capsule pieces is achieved leaving practically no visible mark outside. It ensures availability of a smooth surface that helps to get continous and fluid tight film coating application onto formed capsules.

Capsules for pharmaceutical use come in standard sizes that conform to a numbering system, which indicates their length, diameter and volume. The largest capsule employed for human ingestion is referred to as a size #000, whereas the smallest is a size #5.

A size #000 capsule will typically have a diameter of about 9.9 mm and a locked length of about 26.1 mm. By "locked length" is meant the length of a capsule measured once the two hemispheres of the capsule have been fixed together and sealed.

A size 00 capsule will typically have a diameter of about 8.5 mm and a locked length of about 23.3 mm.

A size 00e1 capsule will typically have a diameter of about 8.5 mm and a locked length of about 25.3 mm.

A size 0 capsule will typically have a diameter of about 7.6 mm and a locked length of about 21.7 mm.

A size 1 capsule will typically have a diameter of about 6.9 mm and a locked length of about 19.4 mm.

A size 2 capsule will typically have a diameter of about 6.3 mm and a locked length of about 18.0 mm.

A size 3 capsule will typically have a diameter of about 5.8 mm and a locked length of about 15.9 mm.

A size 4 capsule will typically have a diameter of about 5.3 mm and a locked length of about 14.3 mm.

A size 5 capsule will typically have a diameter of about 4.9 mm and a locked length of about 11.1 mm.

As stated hereinabove, the dosage form of the present invention is heavier at one of its ends than the other.

The weight bias between the two ends is such that when placed in an aqueous fluid, the dosage form will self-orientate to float with its long axis substantially perpendicular to the surface of the liquid with the relatively heavier end pointing generally downwards into the fluid and the relatively lighter end pointing generally upwards and away from the fluid.

The weight bias may be achieved by means of a weighting agent being applied to one end of the elongate dosage form. The weighting agent may be applied proximal to one end of the dosage form or it may be any where close to one end thereof provided that it is contained within one hemisphere of the dosage form and provided that the dosage form is able to self-orientate and float in the manner described above.

Weighting agents are selected for their high density as well as their physiological inertness. Barium sulphate is a suitable weighting agent, as is dibasic calcium phosphate, iron oxide, iron, titanium dioxide, high density calcium carbonate, in particular calcium carbonate having a density of about 1.3 or greater, calcium sulphate and the like. It is of course optional to use two or more of these weighting agents in combination. Among the above named weighting agents, the most preferred is barium sulphate.

The amount of the weighting agent to be incorporated into a dosage form will depend upon the nature of the weighting agent selected and in particular its density. It should be sufficient to increase the density of the dosage form such that it orientates itself as described above, without causing the dosage form to sink in gastric fluid. In the case of a hollow capsule dosage form, the amount of weighting agent can be easily calculated having regard to the volume of the dosage form. For example, a size #00 gelatin capsule will have a volume of about 0.95 ml and an average weight of 119.mg. Having regard to the amount of drug substance and any excipients present in the dosage form, one can easily calculate the amount of weighting agent to provide the desired effect.

The weight of the weighting agent may range from 10 up to 500 mg, more particularly 10 to 400 mg, still more particularly between 100 and 350 mg, more particularly 50 to 250 mg.

The weighting agent may be formed as an integral part of the dosage form, or it may be applied to it, or be part of its fill in the event that the dosage form is a hollow capsule.

Referring to hollow capsules by way of illustration, the weighting agent may be mixed with capsule-wall forming materials and form part of the capsule; or it may be applied as a coating on the capsule wall. Alternatively, the weighting agent may form part of the filling of the capsule.

As part of the filling, the weighting agent may take the form of a small tablet, minitab, granule, particle, slug or bead, or it may comprise more than one of these. As stated above, the weighting agent should be contained in only one end of the dosage form in order that it can bias the dosage form to float in gastric fluid in the manner described above. As such, the small tablet, granule, particle, slug, bead or the like, can be fixed in the capsule at one end and be substantially prevented from moving from this position.

In a particular embodiment of the invention, the dosage form is in the form of a hollow capsule and the weighting agent is applied in the form of one or more of a small tablet, granule, particle, bead or slug, as part of the fill of said capsule. In a more particular embodiment, the capsule is a size #00 capsule. In a still more particular embodiment, the weighting agent is employed in an amount of 150 to 450 mg, more particularly 50 to 250 mg.

If the weighting agent is applied as part of the fill of a capsule, it may be fixed or adhered to one end of the capsule by means of an adhesive or by frictional engagement with the internal surface of the capsule wall. Alternatively, the capsule may contain an additional filling material, which is adapted to substantially fill the volume of the capsule thereby to retain the weighting agent at one end of the capsule and prevent it from moving or to limit its movement in order that it is retained at one end of the capsule and the capsule remains self-orientating. The additional filling material may take many forms. For example, it may be in the form of wadding, more particularly cotton wadding. The additional filling material may even be in the form of a small plug of a waxy material. The waxy material may have a low melting point to enable it to be poured onto the high density material such that when it solidifies it holds and retains the weighting agent in the correct location in the capsule volume. Materials such as macrogol and natural or semi synthetic lipid waxes may be used for this purpose. The preferred choice is a lipophilic low HLB wax having a melting point above 37° C. In a preferred embodiment the melting point of the material is above 50° C.

In a particular embodiment the additional fill material may be provided in the form of a second capsule, of smaller diameter and length such that it can fit inside of the first capsule whilst leaving the volume between the capsules free in order to receive the weighting agent. This capsule embodiment is shown in FIG. 1.

In a particular embodiment a size #2 capsule may be fitted inside a size #00 capsule to provide a capsule-in capsule dosage form. In this way, there is still sufficient fill volume in the #00 capsule to receive a weighting agent and to prevent the weighting agent from being substantially displaced from one end of said #00 capsule. The skilled person will appreciate however, that other combinations of internal and external capsules are possible, provided that the external capsule is of a size that can be swallowed easily and yet be retained in the stomach by virtue of its size relative to the pyloric sphincter; and the volume between the capsules is sufficiently large as to receive a weighting agent and substantially prevent its movement within this volume.

The dosage forms according to the present invention are intended as vehicles for drug substances. A drug substance may be incorporated in the dosage form in any convenient manner. However, in a particular embodiment the drug substance may be formed as a coating around the dosage form. In a particular embodiment, the dosage form is a capsule, more particularly a capsule-in-a-capsule. The external surface of the capsule is coated with a coating containing a drug substance.

Drug substances useful in the present invention include any physiologically or pharmacologically material that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. The drug substances include inorganic and organic compounds, including, without limitation, those substances which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, the alimentary and excretory systems, the histamine system and the central nervous system.

The Biopharmaceutical Classification System (BCS) introduced by the FDA has categorised drug substances according to their solubility and intestinal permeability. Drug substances that are highly soluble and permeable (Class I) are predicted to be well absorbed when given orally. All other substances (classes II through IV) are either poorly soluble or poorly permeable or both poorly soluble and poorly permeable. These substances would be expected to present challenges to the development of drug products with good bioavailability or with sustained release characteristics. Increasing numbers of drug substances are found in II through IV and many of these display variable absorption in different regions of the GI tract, in particular in the stomach, duodenum and jejunum. Drug substances of this type may be employed in the present invention.

Particular classes of drug substances useful in the present invention are, for example, some active nucleic acids or amino acids and their derivatives, peptidomimetic substances, antiulcer agents, proteins, enzymes, enzyme inhibitors, hormones, polynucleotides, nucleoproteins, polysaccharides, glycoproteins, lipoproteins, peptides, polypeptides, steroids, hypnotics and sedatives, psychic energizers, tranquilizers, antipsychotics, anticonvulsants, antiepileptics, antidepressants, muscle relaxants, antiparkinson agents, anti migraine, analgesics, immunosuppressants, anti-inflammatories, antihistamines, local anesthetics, muscle contractants, antimicrobials, antimalarials, antivirals, antibiotics, antiobesity agents, antidiabetic agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Examples of drug substances useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tolbutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, iloperidone, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, lercanidipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, imipramine and pharmaceutical salts of these active agents.

Further examples are proteins and peptides which include, but are not limited to, cyclosporins such as cyclosporine A, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The present invention is particularly useful to deliver drug substances that are poorly absorbed in the lower gastrointestinal tract, but well absorbed in the upper gastrointestinal tract (i.e., the small intestine) or substances that exhibit poor solubility such that the increased retention time in the stomach allows for a greater quantity of the substance to dissolve from the dosage form than would otherwise be dissolved. Typically, antiviral, antifungal and antibiotic agents, e.g. sulfonamides, quinolones, penicillins, cephalosporins, aminoglycosides, and tetracyclines, are representative classes of substances for which the invention is particularly useful. Such antibiotic agents may include, for example, beta.-lactam antibiotics, vancomycin, clidamycin, erthromycin, trimethoprim-sulfamethoxaazole, rifampin, ciprofloxacin, amoxicillin, clindamycin, ceftriaxone, cefotaxime, chloramphenicol, clindamycin, cefoxitin, doxyclycline, spectinomycin, ofloxacin, rifampin, minocycline, doxycycline, aztreonam, imipenem, meropenem, nitrofurantoin, azithromycin, atovaquone, trimetrexate, dapsone, primaquin, trimetrexate, ketoconazole, fluconazole, amphotericin B, itraconazole, trifluridine, foscarnet, zidovudine amantadine, interferon alfa, sulfonamides such as sulfisoxazole, sulfadiazine, and sulfasalazine, quinolones and fluoroquinolones such as for example, cinoxacin, forfloxacin, diprofloxacin, ofloxacin, spardlosxacin, lomefloxacin, fleroxacin, pefloxacin and amifloxacin, gentamicin, tobramycin, amikacin, netilmicin, kanamycin and neomycin. Representative antiviral agents include acyclovir, famciclovir, foscarnet, ganciclovir, idoxuridine, sorivudine, trifluridine, valacyclovir, vidarabine, didanosine, stavudine, zalcitabine, zidovudine, amantadine, interferons e.g., interferon alpha, ribavirin, rimantadine, nucleoside RT inhibitors, such as lamivudine and adeforvir, non-nucleoside inhibitors such as nevrapine, delavairidine, iviride, saquinavir and indinavir, nucleoside DNAp inhibitors such as famciclovir, fialuridine, cidofovir and lobucavir, antisense oligonucleotides such as afovirsen, receptor decoys such as sICAM-1, capsid binding agents such as pirodavir and neuraminidase inhibitors such as GG167.

Specific examples of drug substances that are readily absorbed in the upper gastrointestinal tract relative to the lower gastrointestinal tract are acyclovir, ganciclovir, cimetidine, ranitidine, captopril, methyldopa, selegiline and the like. Specific examples of active agents that exhibit poor solubility in water are diphenidol, meclizine hydrochloride, prochloperazine maleate, phenoxybenzamine, triethylperazine maleate, anisindone, diphenadione erythrityl tetranitrate, digoxin, isofilurophate, acetazolamide, methazolamide, bendroflumethiazide, chlorpropamide, tolazamide, chlormadionone acetate, phenaglycodol, allopurinol, alluminurri aspirin, methotrexate, acetyl sulfisoxazole, erythromycin, progestins, esterogenic, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiol 3-methyl ether, pednisolone, 17-alpha-hydroxyprogesterone acetate, 19-norprogesterone, norgestrel, norethindrone, progesterone, norgesterone, norethlynodrel, and the like.

Retention of a dosage form of the present invention in the stomach for a prolonged period of time make it especially useful for the localized treatment of gastric acidity and gastrointestinal disorders such as duodenal ulcers, peptic ulcers and chronic gastritis. Representative drug substances for such uses include cimetidine, ranitidine, famotidine, nizatidine, bifentidine, nifentidine, roxatidine, zolentine, omeprazole, lansoprazole antacids such as magnesium carbonate, aluminium carbonate, aluminium hydroxide, magnesium oxide, sucralfate, carbenoloxalone, misoprostol, pirenzepine, telenzepine, bismuth salts, and active agents useful for the treatment of *Helicobacter pylori,* such as metronidazole, timidazole, amoxicillin, clarithromycin, doxycycline, minocycline and tetracycline.

The present invention is particularly suited to the administration of drug substances against *Helicobacter pylori*, e.g., antibiotics as exemplified by minocycline, which are able to penetrate the space between the inner stomach lining and the stomach protective mucous layer, where the *Helicobacter pylori* organism is present, with the result of eradicating the *Helicobacter pylori* organism either totally or to such a degree that relapse after treatment for a large portion of the treatment population is minimized. The increased residence time of the active agent in the stomach provided by this invention permits an active agent delivery period at the site of the organism. The increased efficiency and efficacy of treatment afforded by the present invention allows one to treat gastric disorders in a large number of subjects with dosage forms having a single active agent, preferably minocycline. Accordingly, one avoids the necessity of having to employ complicated treatment regimens directed to the elimination of the *Helicobacter pylori* organism, such as triple drug regimens combining a PPI with two antibiotics.

While for reasons of efficacy, safety, economy, convenience and/or efficiency it may be desirable to utilize a single drug substances in the dosage forms of the present invention, it is to be understood that more than one drug substance may be incorporated into the dosage form of this invention.

The drug substances can be in various forms, such as uncharged molecules, components of molecular complexes or non-irritating, pharmacologically acceptable salts. Also, simple derivatives of the agents (such as ethers, esters, amides, etc) which are easily hydrolyzed by body pH, enzymes, etc, can be employed. Their pharmaceutically acceptable pure isomers may also be used.

The particle size of the drug substance is preferably below 50 microns, more preferably below 10 microns, still more particularly less than 1 micron. The preparation of the drug substance to achieve desirable particle size is well within the purview of the skilled person and can be achieved using any technology known to provide micron or sub micron particle size range known in the art.

In addition to the drug substance, the drug substance-containing coating may comprise excipients that affect the release profile of the drug substance. The excipients may provide for immediate release, sustained release or a mixture of immediate and sustained release.

The term "immediate release" as used in the present invention takes its art-recognised meaning. A coating is considered to act with immediate release if it meets disintegration and/or dissolution requirements for immediate release solid oral dosage forms as set out, for example in the United States Pharmacopoeia.

The dissolution characteristics of an immediate release coating are preferably such that it displays about 75% dissolution within about 60 minutes in a buffered solution at a temperature of 37 degrees centigrade with a paddle speed of 50 rpm using paddle method apparatus no. 2. USP 26/NF 21 ("71 1 Dissolution") describes compendial test methods and apparatus, which enables investigators to assess that the dissolution requirements are met, and this document is also incorporated by reference.

The term "sustained release" used in relation to a coating, means that the coating is adapted to release a drug substance within a certain time, or at a certain location to accomplish a therapeutic objective not possible using a conventional immediate release coating. More particularly, it means that the release of a drug substance is such that the blood plasma levels of the substance are maintained within a therapeutic range and below a toxic level for a relevant period.

Additional excipients are employed in an immediate release and/or sustained release coating to enhance the bulk properties of the coating, e.g mechanical stability and the like. These excipients typically include plasticizers to improve a coating's flexibility, diluents or fillers, binders or adhesives; disintegrants or disintegrating agents, anti-adherents, glidants or lubricants and miscellaneous other adjuvants such as colourants and flavourants.

Suitable plasticizers include glycerin, propylene glycol, polyethylene glycols (e.g., PEG 400 or 900), triacetin, acetylated monoglyceride, citrate esters, and phthalate esters.

Suitable diluents include pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel PH 12, Avicel PH 101 and Avicel PH102; lactose such as lactose monohydrate, lactose anhydrous and Pharmatose DCL 21; dibasic calcium phosphate such as Emcompress; mannitol; starch; sorbitol; fructose; sucrose; and glucose. The diluent is preferably used in an amount of 0.1% to 90% by weight, more particularly 50% by weight, of the drug substance-containing coating.

Suitable lubricants or glidants or anti tacking agents, include for example, fumed silica or colloidal silicon dioxide such as Aerosil 200 or Cab O Sil, talc, bentonite, stearic acid, magnesium stearate, calcium stearate, sodium stearyl fumarate, polyethylene glycol and sodium lauryl sulphate. The lubricant is preferably used in an amount of 0.5 to 10% by weight, in particular 1% by weight, of the drug substance-containing coating.

Suitable binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; waxes, alginic acids and salts thereof; HPC; HPMC; methylcellulose; maltodextrin and dextrin; povidone; gums; starch and modified starches. The binder preferably may be used in an amount of 2 to 10% by weight, more particularly 5% by weight, of the drug substance-containing coating.

Suitable disintegrants include sodium starch glycolate such as Explotab (®), crospovidone such as Kollidon CL, Polyplasdone XL, sodium carboxymethylcellulose, sodium croscarmellose such as AcDiSol and starch. The disintegrant preferably may be used in an amount of 2 to 10% by weight, more particularly 5% by weight, of the drug substance-containing coating.

If sustained release is required, the coating may contain any of the afore-mentioned ingredients or adjuvants in the amounts mentioned. However, in addition the coating should contain a release rate controlling agent.

The term "release rate controlling agent" includes any agent that controls the rate of release of an ingredient in terms of duration or location in order to give a therapeutic effect not possible with a conventional immediate release formulation, and includes hydrophilic polymers, hydrophobic polymers or mixtures thereof, or copolymers thereof, or mixtures of these polymers and copolymers.

Examples of release-rate controlling agents to be used in this invention include hydroxyalkylcellulose, such as hydroxypropylcellulose and hydroxypropylmethylcellulose; poly(ethylene)oxide; alkylcellulose such as ethycellulose and methylcellulose; carboxymethylcellulose; hydrophilic cellulose derivatives; polyethylene glycol; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly(vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

The release-rate-controlling agent preferably includes a hydroxypropyl methylcellulose (HPMC), a hydroxypropyl cellulose (HPC), a poly(ethylene oxide), an ethylcellulose or a combination thereof, preferably present in an amount of 10 to 90% based on the weight of the drug substance-containing coating.

Preferred types of HPMC for use in accordance with the invention are those sold under the trademark Methocel (Dow Chemical Co.). Suitable Methocels include the K grades such as Methocel Kl 5M, Methocel Kl00M, Methocel Kl00LV and Methocel K4M. Other suitable Methocels include the E, F and J grades.

As HPCs there can be those sold under the trademark Klucel (Hercules, Inc.) or equivalents. Suitable Klucels include Klucel LF, Klucel JF, Klucel GF, Klucel MF and Klucel HF.

As poly(ethylene oxide)s there may be mentioned those sold under the trademark Sentry Polyox (Union Carbide Corp.) or equivalents. Suitable Polyoxs include the Polyox WSR grades such as Polyox WSR Coagulant, Polyox WSR-301, Polyox WSR-303, Polyox WSR N-12K, Polyox WSR N-60K, Polyox WSR-1105, Polyox WSR-205 and Polyox WSR N-3000.

As ethylcelluloses for use in accordance with the invention there can be mentioned those sold under the trademark Ethocel (Dow Chemical Co.) or equivalents e g Surelease (Colorcon).

The hydroxypropylmethylcellulose grades preferably have a viscosity (2 wt % solution at 20.degree. C.) of about 5 to 100,000 cps, preferably 4,000 to 100,000 cps. Especially suitable are Methocel K types or their equivalents. The hydroxypropylcelluloses used according to the invention preferably have a number average molecular weight of about 80,000 to 1,150,000, more preferably 80,000 to 600,000.

Polyethylene oxide grades preferably have number average molecular weights of about 100,000 to 7,000,000, more preferably 900,000 to 7,000,000. Especially suitable is Polyox WSR Coagulant, which has a molecular weight of 5,000,000. The ethylcellulose grades used according to the invention preferably have a viscosity of about 3 to 1 10 cps, more preferably 7 to 100 cps.

The drug substance-containing coating may be applied directly to the external surface of the dosage form. However, according to the present invention a pre-coating may be laid down on the dosage form before applying the drug substance-containing coating. A pre-coating may be applied for reasons of increasing the physical stability of the dosage form. In the case of a dosage form in the form of a capsule, a pre-coating may add strength to the capsule, seal it, prevent leakage of ingredients from its fill volume, or protect the capsule from the contents of the stomach.

The pre-coating may be an enteric-coating. An enteric coating, being resistant to gastric fluid, will retain the integrity to the dosage form during the period of release of drug substance.

Enteric coatings are known in the art. An enteric coating comprises a film-forming polymer, which is soluble in an aqueous medium of a pH of higher than 5 but not soluble in an aqueous medium of a pH of about 5 or less. Exemplary enteric polymers include cellulose derivatives, acrylic copolymers, a maleic copolymers, polyvinyl derivatives, shellac and the like.

Particular examples of the cellulose derivative are, for instance, hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate and the like. Among them, hydroxypropylmethylcellulose acetate succinate, hydroxypropylmethylcellulose phthalate and carboxymethylethylcellulose are preferable. Further, hydroxypropylmethylcellulose acetate succinate is more preferable.

Particular examples of acrylic copolymers are, for instance, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer such as Eudragit L100, Eudragit S or Eudragit S100 (each being trade name, commercially available from Röhm Pharma, Germany), methacrylic acid-ethyl acrylate copolymer such as Eudragit L100-55 (trade name, commercially available from Rohm Pharma, Germany), methyl acrylate-methacrylic acid-octyl acrylate copolymer, and the like. Among them, methacrylic acid-methyl methacrylate copolymer is preferable.

Particular examples of maleic copolymers are, for instance, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer and the like.

Particular examples of polyvinyl derivatives are, for instance, polyvinyl alcohol phthalate, polyvinyl acetal phthalate, polyvinyl butylate phthalate, polyvinyl acetoacetal phthalate and the like.

The pre-coating may additionally contain any of the excipients or adjuvants mentioned in relation to the drug substance-containing coating, and in any of the amounts mentioned.

When the dosage form is provided as a capsule, as an alternative to the use of an enteric or partly or wholly insoluble pre-coating, the capsule itself may be endowed with enteric or partly or wholly insoluble properties. In other words, the capsule itself can be rendered impermeable, substantially insoluble or resistant to gastro intestinal secretions. Capsules having enteric or insoluble properties are known in the art. Capsules, for example gelatine capsules, can form insoluble properties by treatment with formaldehyde or gluteraldehyde to decrease the solubility of the capsule wall by crosslinking of the aminoacid chains of gelatin. Alternatively, the capsule wall material may be formed wholly or partly of materials having enteric properties. In the preparation of enteric capsules any of the capsule forming materials or enteric materials useful in the preparation of enteric coatings mentioned above can be employed.

If capsules with enteric properties are employed in the present invention, they may be used with or without the aforementioned pre-coating.

The drug substance-containing coating may be over-coated with a top coating. A top coating may be employed to achieve an aesthetic effect (e.g. an attractive colour or pleasant taste) or information effect, e.g. a coating may be coloured to act as a visual cue for a patient identification of the correct medicament. The top coating may also be used to over-write with information relating to the dosage, or they may elicit a functional effect such as a handling effect, e.g. a smooth coating for ease of swallowing, or a stability effect, e.g. a moisture or light barrier during storage.

The weight of the coating layers can be about 3% to about 95% of the weight of the dosage form based on the total weight of the dosage form.

In order to facilitate the preparation of dosage forms described above there is provided, in a further aspect of the present invention, a process for the preparation of a dosage form described above.

Coatings may be applied by techniques which are conventional for coating in pharmaceutical technology.

In a particular embodiment of the present invention the dosage forms of the present invention may be coated using film coating techniques. Film coating techniques include electrodeposition, pan coating or fluid bed drier coating. Film coating in a vented side pan coater is a preferred coating method of the invention.

Film coating is the deposition of thin films onto a dosage form from solutions that are organic-solvent based or water based. A film coating may be a solution or suspension of polymers and other excipients or adjuvants mentioned hereinabove. Solvents used for the preparation of the coating-dispersion may be any of those known in the art for film coating pharmaceutical dosage forms and include water, ethanol, methanol, propan-2-ol, acetone, ethyl acetate, acetic acid, glycols, dichloromethane, dimehylformamide, dimethylsulfoxide, chloroform, toluene, methylene chloride, benzene, ethoxyethyl acetate, ethylene glycol monoacetate, ethyl lactate, monoethyl acetate, methyl ethyl ketone and their combinations. Among the above-mentioned solvents, a solvent to be used can be selected according to a property of each coating layer and can suitably be used in admixture thereof.

Film coating is particularly suitable for coating capsules.

The major components of a film coating formulation can include, but are not limited to, a polymer, a plasticizer, a colorant, and a solvent. Ideally the polymer is soluble in a wide range of solvent systems and is able to produce coatings with good mechanical stability. Suitable polymers for film coating include, but are not limited to, cellulose ethers, particularly hydroxypropyl methylcellulose, hydroxypropyl cellulose, methylcellulose, sodium carboxymethylcellulose, and acrylics such as methacrylate or methyl methacrylate copolymers. In some embodiments, the polymer used in the coating solution is sodium carboxymethylcellulose. In some embodiments, the polymer used in the coating solution is sodium alginate. In some embodiments, the polymer used in the coating solution is a mixture of sodium carboxymethylcellulose and sodium alginate.

Additionally, any of the excipients or adjuvants referred to above may be employed in any of the coating layers depending on the properties required as described above.

Suitable coating processes include coating pans and fluidized-bed coating equipment as described in Remington: The Science and Practice of Pharmacy, Lippincott Williams & Wilkins, 21st ed. (2005) ("Remington's"). In some embodiments, the coating solution is applied to a capsule using a spray coating technique. Either an air-less spray or an air spray coating technique can be used for film coating as described in Remington's. The use of a spray coating technique permits finely nebulized droplets of the coating solution to be delivered to the capsule surface. These techniques are ideal for commercial production because they ensure uniform coverage of capsules without them sticking together.

In some embodiments, a side-vented coating pan is used to apply the coating solution to the capsule by a spray coating technique. Suitable side-vented coating pans include the Accela-Cota (Thomas Engineering, Hoffman Estates, Ill.), the Fast Coater (O'Hara Manufacturing Ltd., Toronto Canada), the Hi-Coater (Vector Corp., Marion, Iowa), the Driacoater (Driam Metallprodukt, GmbH, Eriskirch, Germany), and the Pro Coater (Glatt Air Techniques, Ramsey, N.J.).

If the dosage form according to the invention is in the form of a capsule, it can be filled with a weighting agent, an additional filling material, in particular another hollow capsule, as described above, before being sealed and then coated as described above.

Filling may be carried out by any means known in the art for filling capsules for pharmaceutical use. By way of example, capsules may be filled by means of an intermittent or continuous motion capsule filling machine equipped with dosators to feed empty capsules with weighting agents, internal capsules or any other materials to be filled. Examples of capsule filling machines are the Zanazi 40 of the company IMA in Bologna and the model MG Futura level 02 of the company MG2 in Bologna. The capsule-in capsule form of a dosage form of the present invention can be realised by means of a manual machine type Zuma 150 or 300 and type Parke-Davis/Capsugel.

The dosage forms of the present invention, in the form of capsules, may be sealed after filling, and optionally before coating, using a sealing means that can be provided around the body of the capsule.

A sealing agent used for the sealing means can be a substance which can make the surface of the capsule at the joint of a body and a cap smooth. Examples of the sealing agent are, for instance, a water-soluble polymer, a water-insoluble polymer, a low pH-soluble polymer, an enteric polymer, a saccharide, a low molecular electrolyte and the like.

As the water-soluble polymer used as the sealing agent, there can be used water-soluble polymers which can be used for the intermediate layer. Examples of the water-soluble polymer are, for instance, a water-soluble polysaccharide ether such as methylcellulose, hydroxypropylcellulose or hydroxypropylmethylcellulose; a water-soluble polyvinyl derivative such as polyvinylpyrrolidone or polyvinylalcohol; a polysaccharide such as pullulan; a polyethyleneglycol; and the like.

Examples of the water-insoluble polymer used as the sealing agent are, for instance, a water-insoluble acrylic copolymer, e.g. ethyl acrylate-methyl methacrylate-trimethylammoniumethyl methacrylate chloride copolymer such as Eudragit RS or Eudragit RL (each being trade name, commercially available from Röhm Pharma, Germany), ethyl acrylate-methyl methacrylate copolymer such as Eudragit NE (trade name, commercially available from Röhm Pharma, Germany) and the like; a water-insoluble cellulose derivative such as ethylcellulose or cellulose acetate; a water-insoluble polyvinyl derivative such as polyvinyl acetate or polyvinyl chloride; and a mixture thereof.

As the saccharide and the low molecular electrolyte used as the sealing agent, there can be used saccharides and low molecular electrolytes which can be used for the intermediate layer. Examples of the saccharide are, for instance, a monosaccharide such as glucose, a disaccharide such as sucrose, and the like, and examples of the low molecular electrolyte are, for instance, an inorganic salt such as sodium chloride, and the like.

The above-mentioned sealing agent can be used alone or in admixture thereof.

In further preferred embodiments, the dosage form of the present invention is advantageously utilised in the treatment of pathologies responsive to pharmacotherapy with drugs having a narrow absorption window. These pathologies are exemplified by the following non exhaustive non limiting list: CNS disorders such as Parkison's disease, Alzheimer's disease, neuropathic pain, epilepsy, depression, insomnia, psychiatric disorders and others; infectious diseases, including viral infections such as herpes infections, hepatitis infections and AIDS; metabolic diseases such as diabetes, dislipidemia and others; endocrinologic disorders including reproductive disorders;cardiovascular disorders such as hypertension and CHF, coagulation disorders and others; renal disorders such as renal failure, pyelonephritis and others; musculoskeletal system disorders such as osteoporosis, myasthenia gravis and others; pulmonary disorders such as pulmonary arterial hypertension, asthma, COPD and others; benign and malignant cancers, auto immune diseases; and other indications whereby administration of drugs suitable for the system of the present invention is advantageous to treat patient pathological conditions.

FIG. 1: Represents a schematic view of a dosage form (1) according to the present invention. The dosage form (1) comprises an outer capsule (2) that is, size #00 for example, that contains an intermediate coating (3) applied to the outer surface of capsule (2), and an outer coating (4) containing a drug substance that is applied to the intermediate coating (3). Located within the volume of outer capsule (2) is a weighting agent (5) that is located at one end of the fill volume of capsule (2). Occupying substantially the remainder of the fill volume of the capsule (2) is an inner capsule (6) of size #2, for example. By means of this inner capsule (6) the weighting agent (5) is retained in a position at one end of the dosage form.

Figure 2:
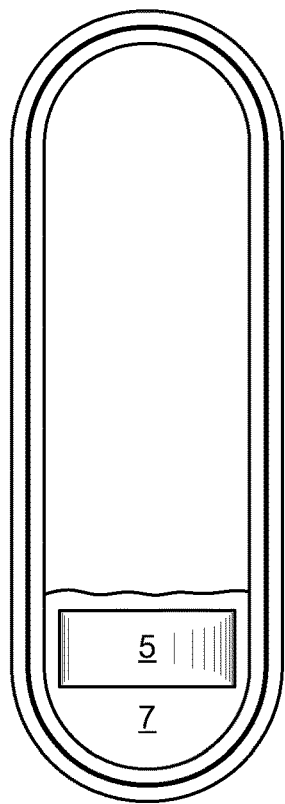

FIG. 2: Represents a schematic view of a dosage form according to the present invention that is substantially identical to the dosage form of FIG. 1 save for the omission of the inner capsule (6) and in its place a plug (7) of waxy material that completely encases the weighting agent (5) retaining the weighting agent at one end of the fill volume of capsule (2).

Figure 3:
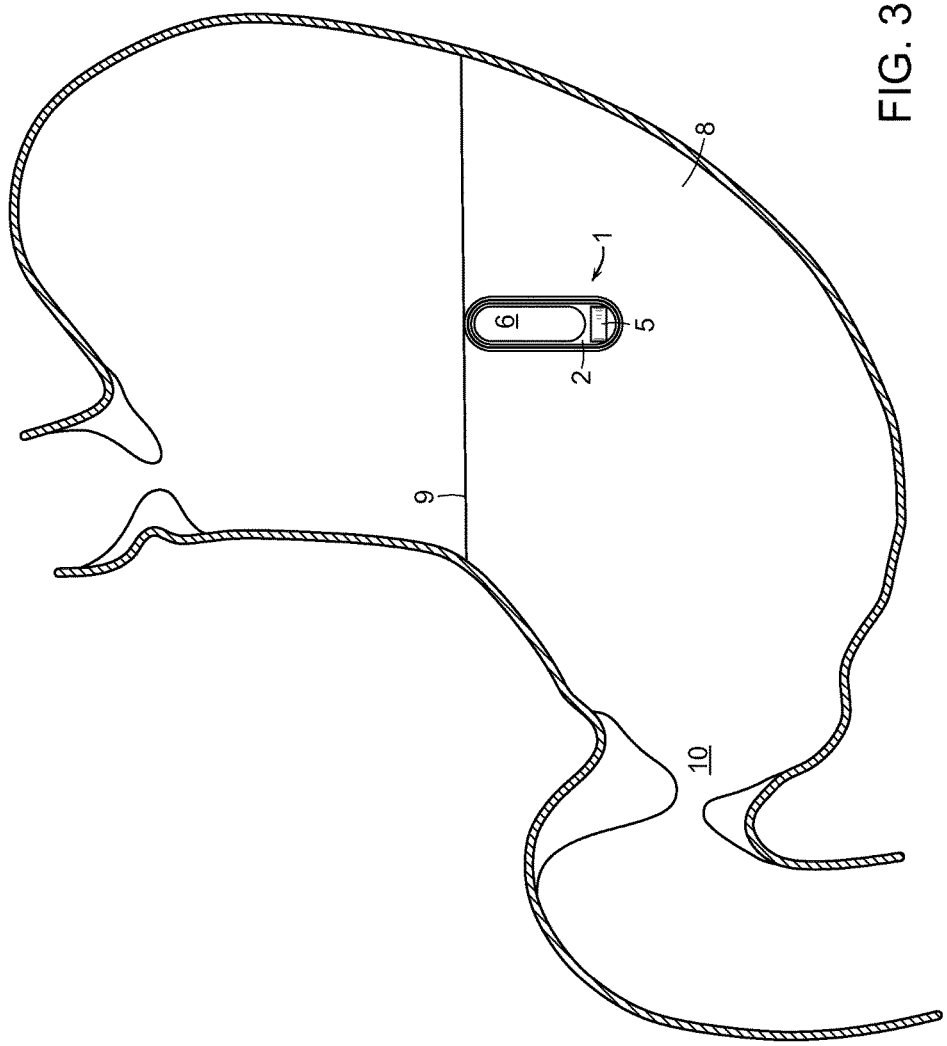

FIG. 3: Represents a schematic view of a dosage form of FIG. 1 in a stomach. The dosage form (1) is shown floating in stomach contents (8) in such a way that the long axis of the capsule is substantially perpendicular to the surface (9) of the stomach contents. The dosage form aligns itself in this manner because of the presence of the weighting agent (5) is retained at one end of the outer capsule (2) by means of the inner capsule (6). As the stomach contents are drained from the stomach, the dosage form retains its substantially perpendicular alignment preventing it from passing through the pylorus (10).

Figure 4:
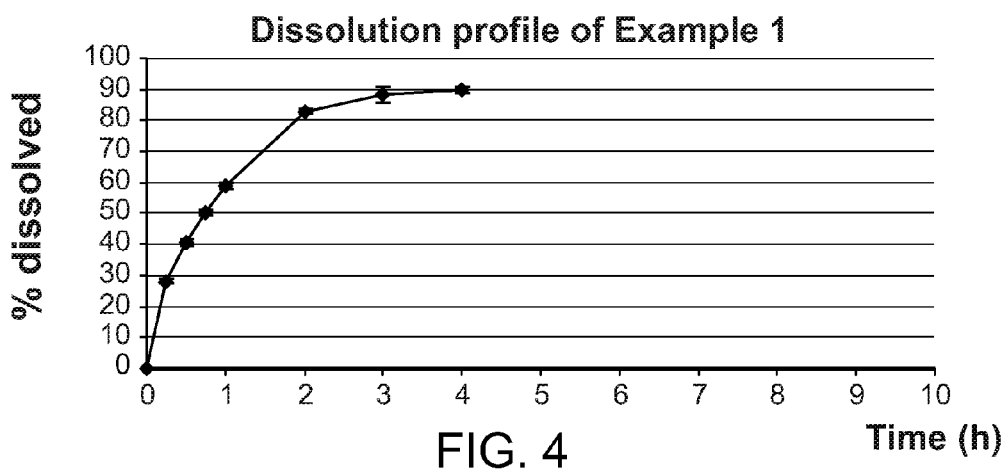

FIG. 4: Shows the dissolution profile of the dosage form of Example 1.

Figure 5:
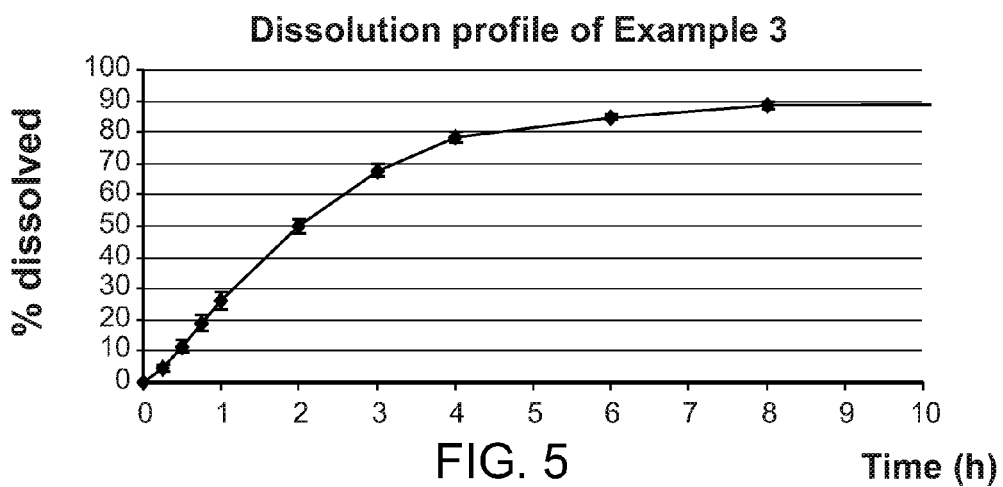

FIG. 5: Shows the dissolution profile of the dosage form of Example 3.

Figure 6:
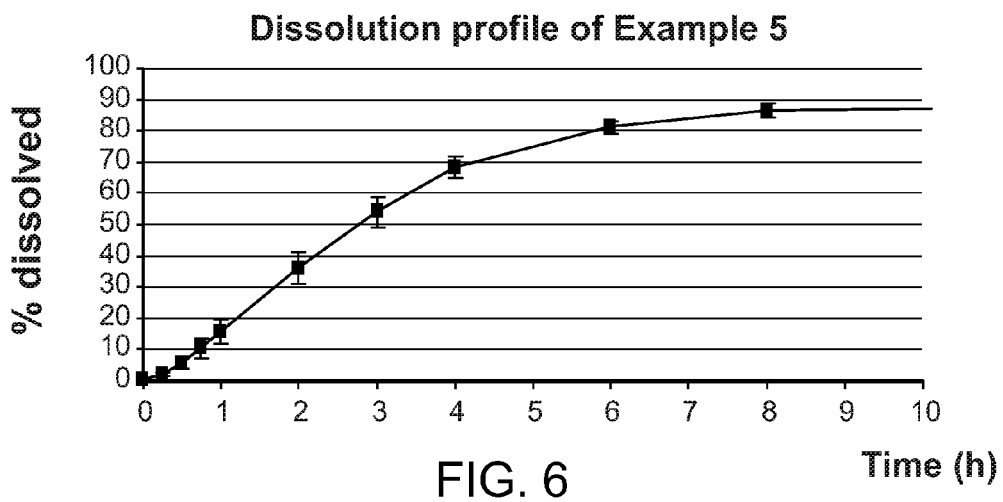

FIG. 6: Shows the dissolution profile of the dosage form of Example 5.

Figure 7:
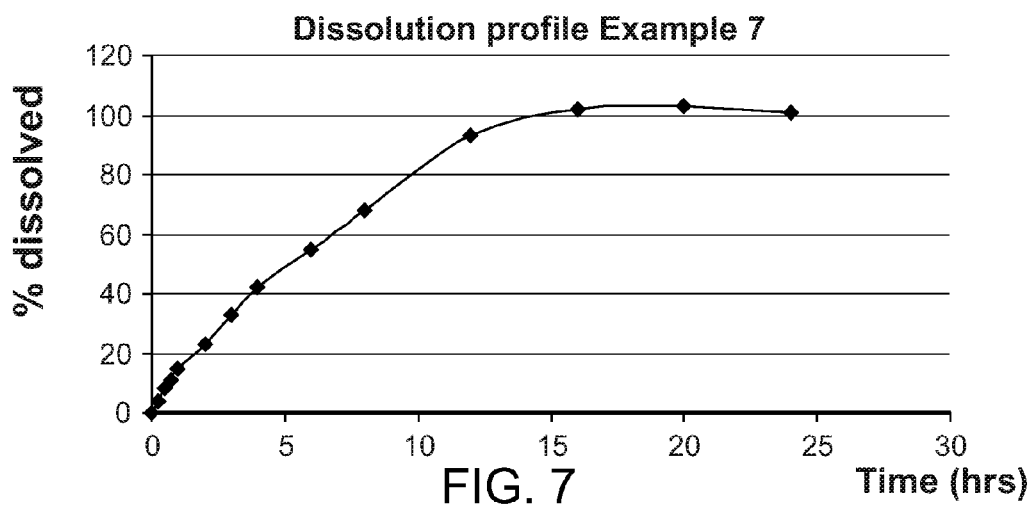

FIG. 7: Shows the dissolution profile of the dosage form of Example 7.

Figure 8:
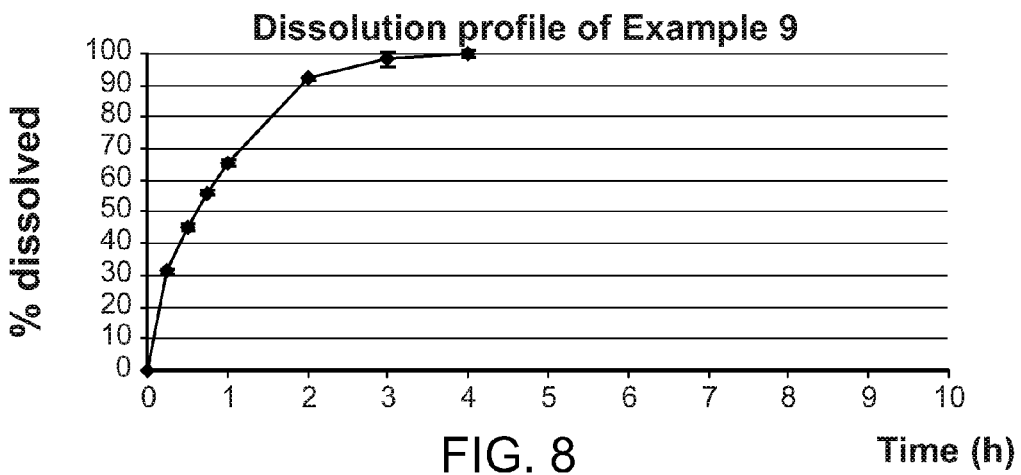

FIG. 8: Shows the dissolution profile of the dosage form of Example 9.

Figure 9:
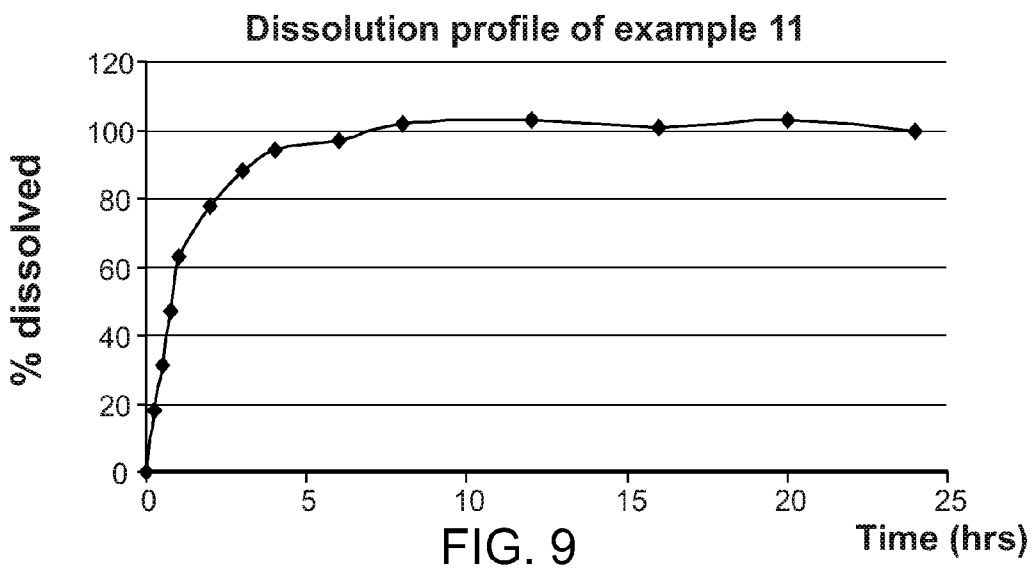

FIG. 9: Shows the dissolution profile of the dosage form of Example 11.

Figure 10:
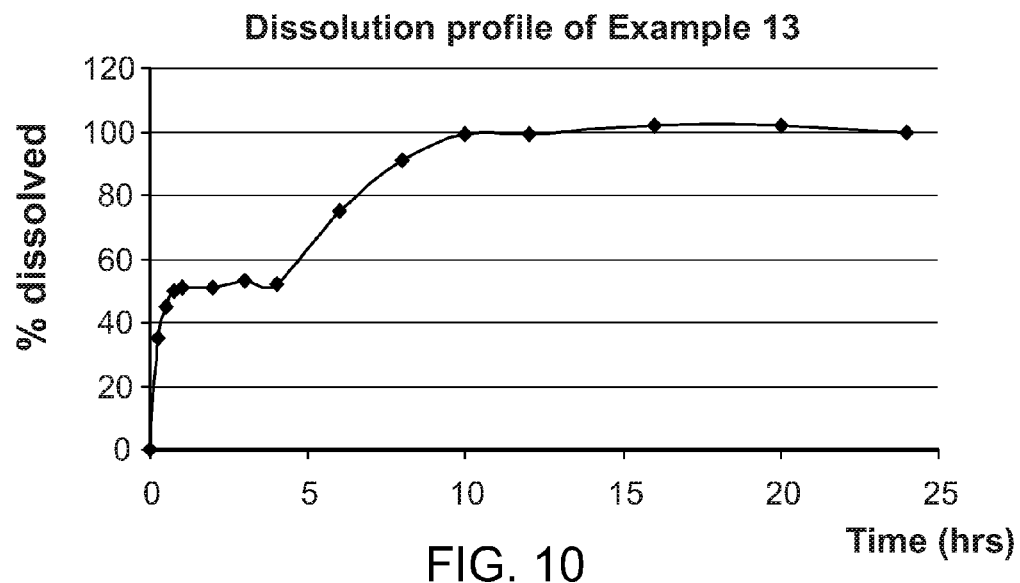

FIG. 10: Shows the dissolution profile of the dosage form of Example 13.

Figure 11:
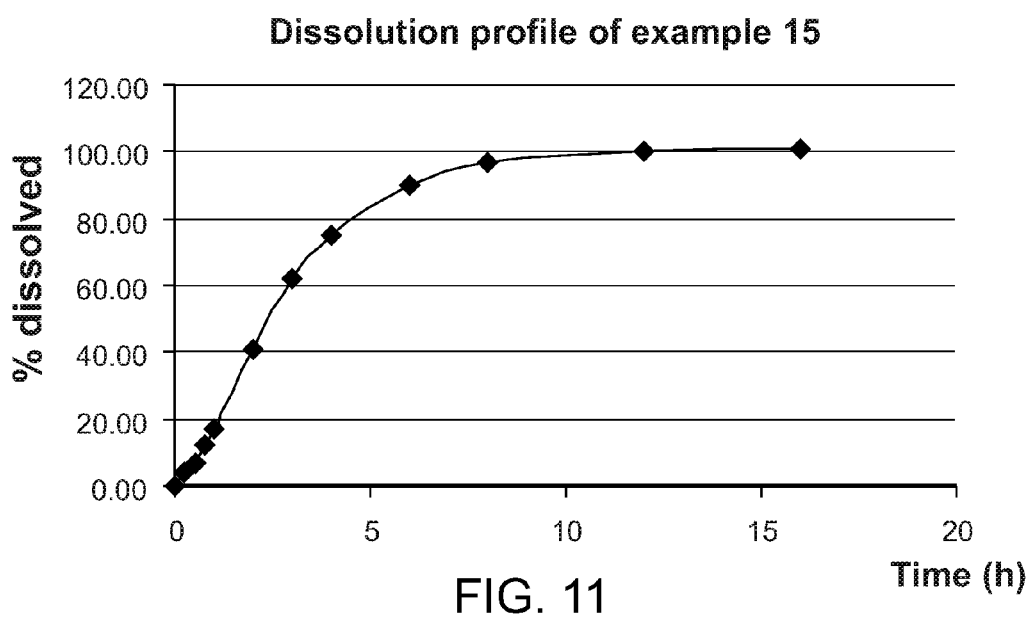

FIG. 11: Shows the dissolution profile of the dosage form of Example 15.

There now follows a series of examples, which serve to illustrate the invention.

Example 1

Tablets of 100 mg of barium sulphate having a diameter of 5.75 mm are prepared by first mixing barium sulphate with Prosolv (silicified microcrystalline cellulose) then addition of magnesium stearate. Finally the blend is tabletted with 5.75 mm diameter tooling.

Then one barium sulphate tablet per capsule is inserted in a size 1 gelatin capsule and a size 3 gelatine capsule is added before closure of the size 1 gelatin capsule. The size 1 capsules are then sealed with Quali-seal apparatus using an aqueous solution of gelatine (20&w/w) at 60° C. (about 5 mg of gelatine-dry matter is applied).

In a vented side pan coater, a first layer of an aqueous solution consisting of Eudragit RS30D, TriEthylCitrate (TEC) and talc is applied onto the filled size 1 capsule. The quantity of dry matter applied to the capsule is 16.8 mg of Eudragit R30D, 3.3 mg of TEC and 8.4 mg of talc. This layer provides capsule water tightness for a duration up to 24 hours.

A second layer is then applied by spraying an aqueous solution of ropinirole hydrochloride in sufficient quantity to get 75 mg of ropinirole HCl per size 1 capsule.

The composition of the aqueous solution of ropinirole HCl is the following:

| | |
|---|---|
| Eudragit RS 30 D (as suspension) | 23.91% |
| Eudragit RL 30D (as suspension) | 5.98% |
| TEC | 1.79% |
| Talc | 4.48% |
| Ropinirole HCl | 8.54% |
| Purified Water | QS 100% |

Example 2

Capsules from Example 1 are tested in USP dissolution apparatus 2 at 100 rpm in 900 ml acetate buffer (pH 4.5).

Dissolution profiles are presented in FIG. 4.

The dosage form of Example 1 remains buoyant for more than 24 hours

Example 3

A capsule from Example 1 is further coated with a polymeric layer for a weight gain of 22.5 mg. The solution sprayed onto the capsule from Example 1 has the following composition:

| | |
|---|---|
| Eudragit RS 30 D (as suspension) | 31.38% |
| Eudragit RL 30D (as suspension) | 7.84% |
| TEC | 2.35% |
| Talc | 5.88% |
| Purified Water | QS 100% |

Example 4

Capsules from Example 3 are tested in USP dissolution apparatus 2 at 100 rpm in 900 ml acetate buffer (pH 4.5).

Dissolution profiles are presented in FIG. 5.

The capsules of Example 3 remain buoyant for more than 24 hours

Example 5

A capsule from Example 1 is further coated with a polymeric layer for a weight gain of 43 mg. The solution sprayed onto the capsule from Example 1 has the following composition:

| | |
|---|---|
| Eudragit RS 30 D (as suspension) | 31.38% |
| Eudragit RL 30D (as suspension) | 7.84% |
| TEC | 2.35% |
| Talc | 5.88% |
| Purified Water | QS 100% |

Example 6

Capsules from Example 5 are tested in USP dissolution apparatus 2 at 100 rpm in 900 ml acetate buffer (pH 4.5).

Dissolution profiles are presented in FIG. 6.

The invention from Example 5 remains buoyant for more than 24 hours.

Example 7

Tablets of 100 mg of barium sulphate having a diameter of 5.75 mm are prepared in a manner described in Example 1 above. Then one tablet per capsule is inserted in a size 1 gelatine capsule. A size 3 gelatine capsule is added before closure of the size 1 gelatine capsule. Size 1 capsules are then sealed with Quali-seal apparatus using a aqueous solution of gelatine (20&w/w) at 60° C. (about 5 mg of gelatine—dry matter—is applied).

In a vented side pan coated, a first layer of an aqueous solution consisting of Eudragit RS30D, TriEthylCitrate (TEC) and talc is applied onto the filled size 1 capsule. The quantity of dry matter applied by capsule is 16.8 mg of Eudragit R30D, 3.3 mg of TEC and 8.4 mg of talc. This layer provides capsule water tightness for a duration up to 24 hours.

A second layer is then applied by spraying an nanosuspension of fenofibrate in sufficient quantity to get 145 mg fenofibrate per size 1 capsule.

The composition of the aqueous nanosuspension of fenofibrate is the following:

| | |
|---|---|
| Eudragit RS 30 D (as suspension) | 23.91% |
| Eudragit RL 30D (as suspension) | 5.98% |
| TEC | 1.79% |
| Talc | 4.48% |
| Vit E TPGS | 0.9% |
| Fenofibrate | 16.8% |
| Purified Water | QS 100% |

Example 8

Capsules from Example 7 are tested in USP dissolution apparatus 2 at 100 rpm in 900 ml 1% SLS solution.

Dissolution profiles are presented in FIG. 7.

The capsules of Example 7 remain buoyant for more than 24 hours.

Example 9

Tablets of 100 mg of barium sulphate having a diameter of 5.75 mm are prepared substantially as described in Example 1 above. Then one tablet per capsule is inserted in a size 1 gelatine capsule, molten hydrogenated castor oil is poured on the barium sulphate tablet, before being left to cool before closure of the size 1 gelatin capsule.

The size 1 capsules are then sealed with Quali-seal apparatus using an aqueous solution of gelatine (20&w/w) at 60° C. (about 5 mg of gelatine-dry matter is applied).

In a vented side pan coater, a first layer of an aqueous solution consisting of Eudragit RS30D, TriEthylCitrate (TEC) and talc is applied onto the filled size 1 capsule. The quantity of dry matter applied by capsule is 16.8 mg of Eudragit R30D, 3.3 mg of TEC and 8.4 mg of talc.

This layer provides capsule water tightness for a duration of up to 24 hours.

A second layer is then applied by spraying an aqueous solution of ropinirole hydrochloride in sufficient quantity to get 75 mg of ropinirole HCl per size 1 capsule.

The composition of the aqueous solution of ropinirole HCl is the following:

| | |
|---|---|
| Eudragit RS 30 D (as suspension) | 23.91% |
| Eudragit RL 30D (as suspension) | 5.98% |
| TEC | 1.79% |
| Talc | 4.48% |
| Ropinirole HCl | 8.54% |
| Purified Water | QS 100% |

Example 10

Capsules from Example 9 are tested in USP dissolution apparatus 2 at 100 rpm in 900 ml acetate buffer (pH 4.5).

Dissolution profiles are presented in FIG. 8

The capsules from Example 8 remain buoyant for more than 24 hours.

Example 11

A capsule prepared according to Example 3 is further coated with a ropinirole HCl solution in order to get 50 mg of ropinirole HCl applied.

The formulation of the ropinirole HCl solution is the following:

| | |
|---|---|
| Ropinirole HCl | 12% |
| Opadry II | 12% |
| Purified water | QS 100% |

Example 12

Capsules from Example 11 are tested in USP dissolution apparatus 2 at 100 rpm in 900 ml acetate buffer (pH 4.5).

Dissolution profiles are presented in FIG. 9.

The invention from Example 11 remains buoyant for more than 24 hours.

Example 13

(Capsule for double pulse release)

In a vented side pan coater capsules from Example 1 are further coated with a dispersion of hydroxypropyl (25%) and hydroxymethylpropyl (4%) cellulose in an aqueous/ethanolic solution (85% alcohol V/V). Thereafter, a dispersion of ropinirole HCl (15%) in a aqueous/ethanolic solution (85% ethanol V/V) is sprayed until a quantity of 75 mg of ropinirole HCl/capsule has been applied.

Example 14

Capsules from Example 13 are tested in USP dissolution apparatus 2 at 100 rpm in 900 ml acetate buffer (pH 4.5). Dissolution profiles are presented in FIG. 10.

The capsules of Example 13 remain buoyant for more than 24hours.

Example 15

Tablets of 100 mg of barium sulphate having a diameter of 5.75 mm are prepared by first mixing barium sulphate with Prosolv (silicified microcristallin cellulose) then addition of magnesium stearate. Finally the blend is tabletted with 5.75 mm diameter tooling.

Then one barium sulphate tablet per capsule is inserted in a size 1 gelatin capsule and a size 3 gelatine capsule is added before closure of the size 1 gelatin capsule. The size 1 capsules are then sealed with Quali-seal apparatus using an aqueous solution of gelatine (20&w/w) at 60° C. (about 5 mg of gelatine-dry matter is applied).

In a vented side pan coater, a first layer of an aqueous solution consisting of Eudragit RS30D, TriEthylCitrate (TEC) and talc is applied onto the filled size 1 capsule. The quantity of dry matter applied to the capsule is 16.8 mg of Eudragit R30D, 3.3 mg of TEC and 8.4 mg of talc. This layer provides capsule water tightness for a duration of up to 24 hours.

A second layer is then applied by spraying an nanosuspension of iloperidone in sufficient quantity to get 24 mg of iloperidone per size 1 capsule.

The composition of the nanosuspension of iloperidone is the following:

| | |
|---|---|
| Eudragit RS 30 D (as suspension) | 23.91% |
| Eudragit RL 30D (as suspension) | 5.98% |
| TEC | 1.79% |
| Talc | 4.48% |
| Fumaric acid | 6.32% |
| Iloperidone | 6.32% |
| Purified Water | QS 100% |

Then the capsuke is further coated with a polymeric layer for a weight gain of 61 mg. The polymeric solution sprayed onto the capsule has the following composition:

| | |
|---|---|
| Eudragit RS 30 D (as suspension) | 31.38% |
| Eudragit RL 30D (as suspension) | 7.84% |
| TEC | 2.35% |
| Talc | 5.88% |
| Purified Water | QS 100% |

Example 16

Capsules from Example 15 are tested in USP dissolution apparatus 2 at 100 rpm in 900 ml citrate buffer (pH 4.5).

Dissolution profiles are presented in FIG. 11.

The invention from Example 15 remains buoyant for more than 24 hours.

The invention claimed is:

1. An elongate dosage form of cylindrical shape in the form of a hollow capsule which is impermeable to gastro intestinal secretions and having a fill volume inside containing a weighting agent in the form of a tablet comprising dibasic calcium phosphate which is retained at one end of the fill volume, the dosage form being coated with a coating material comprising a drug substance.

2. The dosage form of claim 1, wherein the coating material is in direct contact with the external surface of the dosage form.

3. The dosage form of claim 1, wherein the coating material is in direct contact with a pre-coating material, the pre-coating material being in direct contact with the external surface of the dosage form.

4. The dosage form of claim 3, wherein the pre-coating material is an enteric coating material.

5. The dosage form of claim 2, wherein the coating material further comprises a binder or a release rate controlling agent, or both.

6. The dosage form of claim 3, wherein the coating material further comprises a binder or a release rate controlling agent, or both.

7. The dosage form of claim 4, wherein the coating material further comprises a binder or a release rate controlling agent, or both.

8. The dosage form of claim 5, wherein the binder is selected from a hydroxypropyl cellulose (HPC) and a hydroxypropyl methylcellulose (HPMC).

9. The dosage form of claim 6, wherein the binder is selected from a hydroxypropyl cellulose (HPC) and a hydroxypropyl methylcellulose (HPMC).

10. The dosage form of claim 7, wherein the binder is selected from a hydroxypropyl cellulose (HPC) and a hydroxypropyl methylcellulose (HPMC).

11. The dosage form of claim 5, wherein the release rate controlling agent is in the form of a hydrophilic polymer, a hydrophobic polymer, or mixtures thereof, or copolymers thereof, or mixtures of these polymers and copolymers.

12. The dosage form of claim 6, wherein the release rate controlling agent is in the form of a hydrophilic polymer, a hydrophobic polymer, or mixtures thereof, or copolymers thereof, or mixtures of these polymers and copolymers.

13. The dosage form of claim 7, wherein the release rate controlling agent is in the form of a hydrophilic polymer, a hydrophobic polymer, or mixtures thereof, or copolymers thereof, or mixtures of these polymers and copolymers.

14. The dosage form of claim 11, wherein the release rate controlling agent includes a hydroxypropyl methylcellulose (HPMC), a hydroxypropyl cellulose (HPC), a poly(ethylene oxide), an ethylcellulose, or a combination thereof.

15. The dosage form of claim 12, wherein the release rate controlling agent includes polyethylene glycol, ethycellulose, cellulose acetate phthalate, or a combination thereof.

16. The dosage form of claim 13, wherein the release rate controlling agent includes a hydroxypropyl methylcellulose (HPMC), a hydroxypropyl cellulose (HPC), a poly(ethylene oxide), an ethylcellulose, or a combination thereof.

17. The dosage form of claim 11, wherein the release rate controlling agent includes polyethylene glycol, ethycellulose, cellulose acetate phthalate, or a combination thereof.

18. The dosage form of claim 12, wherein the release rate controlling agent includes a hydroxypropyl methylcellulose (HPMC), a hydroxypropyl cellulose (HPC), a poly(ethylene oxide), an ethylcellulose, or a combination thereof.

19. The dosage form of claim 13, wherein the release rate controlling agent includes polyethylene glycol, ethycellulose, cellulose acetate phthalate, or a combination thereof.

20. The dosage form of claim 1, which is formed of two parts sealed together prior to coating with the coating material comprising a drug substance.

21. The dosage form of claim 1, wherein the fill volume includes a wadding, a plug of waxy material, or a second capsule.

22. The dosage form of claim 1, wherein the dosage form has a length of 15mm or greater along its long axis.

23. The dosage form of claim 22, wherein the length is not longer than 30 or 31 mm.

24. An elongate dosage form of cylindrical shape in the form of a hollow capsule which is impermeable to gastro intestinal secretions and having a fill volume inside containing a weighting agent in the form of a tablet comprising dibasic calcium phosphate which is retained at one end of the fill volume, the fill volume further comprising a wadding, a plug of waxy material, or a second capsule, and the dosage form being coated with a coating material comprising a drug substance.

25. An elongate dosage form of cylindrical shape in the form of a hollow capsule which is impermeable to gastro intestinal secretions and having a fill volume inside containing a weighting agent in the form of a tablet comprising dibasic calcium phosphate which is retained at one end of the fill volume, the dosage form having a length of 15 mm or greater, and the dosage form being coated with a coating material comprising a drug substance.

26. The dosage form of claim 25, wherein the length is not longer than 30 or 31 mm.

* * * * *